(12) United States Patent
Hilgers et al.

(10) Patent No.: US 6,340,464 B1
(45) Date of Patent: *Jan. 22, 2002

(54) ADJUVANTS FOR VACCINES

(75) Inventors: Luuk Hilgers, Utrecht (NL); Michel Strebelle, Brussels (BE)

(73) Assignee: American Cyanamid Company, Madison, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/860,456
(22) PCT Filed: Dec. 21, 1995
(86) PCT No.: PCT/BE95/00118
§ 371 Date: Sep. 30, 1997
§ 102(e) Date: Sep. 30, 1997
(87) PCT Pub. No.: WO96/20007
PCT Pub. Date: Jul. 4, 1996

(30) Foreign Application Priority Data

Dec. 27, 1994 (BE) .................................... 09401173

(51) Int. Cl.$^7$ ..................... A61K 45/00; A61K 47/00; A61K 47/32; A61K 47/30
(52) U.S. Cl. ............... 424/280.1; 424/278.1; 424/184.1; 424/214.1; 424/222.1; 424/486; 424/487; 514/772.6; 514/772.7
(58) Field of Search .................. 424/278.1, 184.1, 424/816, 489, 486, 214.1, 222.1, 280.1; 514/772.6, 772.7

(56) References Cited

U.S. PATENT DOCUMENTS 3,920,811 A * 11/1975 Lund ........................... 424/88
4,340,726 A * 7/1982 Simon et al. ............... 536/17.4
5,047,238 A * 9/1991 Acree et al. ................... 424/89
5,242,686 A * 9/1993 Chu et al. ..................... 424/88
5,565,209 A * 10/1996 Rijke .......................... 424/423
5,883,262 A * 3/1999 Shuto et al. .............. 548/364.1

FOREIGN PATENT DOCUMENTS

DE 161050 * 5/1994
EP 0283085 * 9/1988
EP 0549074 * 6/1993

OTHER PUBLICATIONS

Hilgers et al. Immunology 60: 141–146, abstract (X), 1987.*
Oka et al. Vaccine 8: 573–576, 1990.*
Diamantstein et al. Eur. J. Immunol. 1: 340–343, 1971.*
Kreuter et al. Infect. Immun. 19: 667–675 (A), 1978.*
Kreuter et al. Exp. Cell. Biol 44: 12–19 (B), 1976.*
Kreuter et al. J. Pharm. Sci. 65: 1624–1627 (C), 1976.*
Kreuter et al. Vaccine 6: 253–256 (D), 1988.*
Brugh et al. Am. J. Vet. Res. 44: 72–75, abstract, 1983.*
Wong et al. Australian J. Biol. Sci. 39: 99–108, 1986.*
Skibinski et al. Arch. Immunol. Ther. Exp. 26: 77–83, 1979.*
Kreuter et al. Infect. Immun. 13: 204–210, abstract, 1976.*
Kreuter et al. Med. Microbiol. Immunol. 165: 111–117, 1978.*

* cited by examiner

Primary Examiner—S. Devi
(74) Attorney, Agent, or Firm—John F. Levis

(57) ABSTRACT

Vaccine adjuvants comprising a liquid medium contain polymers with anionic constitutive repeating units and hydrophobic constitutive repeating units. Advantageously, the adjuvants are aqueous solutions of partially esterified polyacrylic acids. The novel adjuvants are highly stable, effective and have a relatively low level of local toxicity. Further, vaccines comprising such adjuvants and a process for producing them are described.

18 Claims, No Drawings

ADJUVANTS FOR VACCINES

The present invention relates to novel vaccine adjuvants. administered, for example, parenterally, induces an immune response, including the production of antibodies. Antibodies are substances contained in the blood and other fluids of the body, as well as in the tissues, and which bind to the antigen to make it innocuous. Antibodies constitute one of the natural defense mechanisms of the body. They are highly specific and they can kill, bind or make innocuous the antigen which has induced their formation.

The antigen, in contact with the immune system, thus activates a complex series of cellular interactions to eliminate the antigen and/or to reestablish the preceding equilibrium.

Two of the characteristic features of antigens are their immunogenicity, that is, their capacity to induce an immune response in vivo (including the formation of specific antibodies), and their antigenicity, that is, their capacity to be selectively recognized by the antibodies whose origins are the antigens.

It is known that it is possible to stimulate the immune response deliberately by administrating a specific antigen by means of a vaccine. This procedure allows the development in the organism of a state of immunologic memory which ensures a more rapid and more effective response of the organism during subsequent contact with the antigen.

However, some antigens have only a weak immunogenicity and they induce an insufficient immune response to procure an effective protection for the organism.

The immunogenicity of an antigen can be increased by administering it in a mixture with substances, called adjuvants, which increase the response against the antigen either by directly acting on the immunological system or by modifying the pharmacokinetic characteristics of the antigen and by thus increasing the interaction time between the latter with the immune system.

The most widespread adjuvants are, on the one hand, Freund's adjuvant, an emulsion comprising dead mycobacteria in a saline solution within mineral oil and, on the other hand, Freund's incomplete adjuvant, which does not contain mycobacteria.

These adjuvants are capable of either increasing the intensity of the immune response to the antigen or of producing an aspecific activation of the immune system.

However, the use of these adjuvants comprises drawbacks such as the formation of irritation or abscess at the point of injection. In addition, for these adjuvants to be effective, the concentration used must be greater than 50% of the injected volume, which limits the useful load of antigens which one can inject in one dose.

The high viscosity of these standard adjuvants based on oil and water make their use impractical because they are difficult to introduce into syringes and inject into the animals.

Another type of adjuvant which has been described comprises a solution of polyacrylic acid (Diamanstein et al., Z. Klin. Chem. Klin. Biochem., Vol. 8, pp. 632–636 (1970) and Diamanstein et al., Eur. J. Immunol., Vol. 1, pp. 335–339 (1971)). The advantage of this type of adjuvant is that it is less viscous than the conventional adjuvants based on mineral oil and water. It can therefore be manipulated and injected more easily. However, the efficacy of these adjuvants is not comparable to that of adjuvants based on water in mineral oil (W/O).

The purpose of the present invention is to propose an adjuvant for vaccines which is effective in a small concentration and without mineral oil.

This purpose is achieved by a vaccine adjuvant comprising an aqueous solution of polymers having anionic constitutive repeating units and hydrophobic constitutive repeating units.

The term anionic constitutive repeating units denotes, for the purposes of the present invention, monomer units, which constitute the polymer, containing groups capable of dissociating into water while forming anions.

Examples of such monomer units which are of use in the present invention to form the anionic constitutive repeating units are (selected from) acrylic acid, methacrylic acid, maleic acid, fumaric acid, ethylenesulfonic acid, vinylsulfuric acid, styrenesulfonic acid, vinylphenylsulfuric acid, 2-methacryloyloxyethanesulfonic acid, 3-methacryloyloxy-2-hydroxypropanesulfonic acid, 2-acryl-2-methylpropanesulfonic acid, 3-acrylamido-3-methylbutanoic acid, 3-methacrylamido-3-methylbutanoic acid, vinylphosphoric acid, 4-vinylbenzoic acid, 3-vinyloxypropane-1-sulfonic acid and N-vinylsuccimidic acid.

Preferably, the monomer units of this type are selected from acrylic acid, methacrylic acid, maleic acid, fumaric acid, ethylenesulfonic acid, vinylsulfuric acid and styrenesulfonic acid.

It is preferred for the monomer units of this type to be selected from acrylic acid, methacrylic acid, maleic acid and fumaric acid.

It is particularly preferred for the monomer units of this type to be acrylic acid units.

The term hydrophobic constitutive repeating units denotes, for the purposes of the present invention, monomer units, which constitute the polymer, containing exclusively hydrophobic groups, also called lipophilic, which do not dissociate in water.

Examples of such monomer units which are of use in the present invention to form the hydrophobic constitutive repeating units are (selected from) alkyl esters, cycloalkyl esters and hydroxyalkyl esters of the above-mentioned acids (acrylic acid, methacrylic acid, maleic acid, fumaric acid, ethylenesulfonic acid, vinylsulfuric acid, styrenesulfonic acid, vinylphenylsulfuric acid, 3-methacryloyloxy-2-hydroxypropanesulfonic acid, 2-methacryloyloxyethanesulfonic acid, 2-acryl-2-methylpropanesulfonic acid, 3-acrylamido-3-methylbutanoic acid, 3-methacrylamido-3-methylbutanoic acid, vinylphosphoric acid, 4-vinylbenzoic acid, 3-vinyloxypropane-1-sulfonic acid or N-vinylsuccimidic acid), and ethers (for example, methoxymethyl, ethoxyethyl, allyloxymethyl, 2-ethoxyethoxymethyl, benzyloxymethyl, cyclohexylmethyl, 1-ethoxyethyl, 2-ethoxyethyl, 2-butoxyethyl, methoxymethoxyethyl, methoxyethoxyethyl, 1-butoxypropyl, 1-ethoxybutyl, tetrahydrofurfuryl or furfuryl ethers).

Preferably, the monomer units of this type are selected from the alkyl esters of acrylic acid, methacrylic acid, maleic acid, fumaric acid, ethylenesulfonic acid, vinylsulfuric acid or styrenesulfonic acid.

Preferably, the monomer units of this type are selected from the alkyl esters of acrylic acid, methacrylic acid, maleic acid or fumaric acid whose alkyl group contains 4–8 carbon atoms.

It is particularly preferred for the monomer units of this type to be linear alkyl esters of acrylic acid whose alkyl group contains 4–8 carbon atoms.

It is particularly preferred for the adjuvants used according to the present invention to be aqueous solutions of polymers whose monomer units used to form the anionic constitutive repeating units consist of acrylic acid, and whose monomer units used to form the hydrophobic constitutive repeating units are selected from linear alkyl esters of acrylic acid whose alkyl group contains 4–8 carbon atoms.

The humoral response to the Vaccines which comprise an aqueous solution of polymers having anionic constitutive repeating units and hydrophobic constitutive repeating units is greater than the response induced by polymers having exclusively anionic constitutive repeating units, such as, for example, the polyacrylic acids.

Indeed, the efficacy of the adjuvants according to the present invention is comparable to that of the standard adjuvants based in water in mineral oil, whereas, in general, their toxicity is much lower.

The adjuvants according to the present invention therefore do not pose any instability problems, as do the standard adjuvants based on an emulsion of oil in water (O/W) or water in oil (W/O), because the latter are always sensitive to stabilizing factors such as the salt concentration, the temperature, etc., which is not the case for the adjuvants for the present invention. Their stability, in principle, corresponds to the stability of the polymers exclusively containing anionic constitutive repeating units, such as the polyacrylic acids.

One of the advantages of the adjuvant according to the present invention is that it is effective at a weak dose. It is therefore possible to increase the load of antigens per volume injected. In the vaccines based on W/O, the mineral oil occupies approximately 50% of the volume of the vaccine, whereas the volume fraction occupied by the adjuvants according to the present invention (for example, based on polyacrylic acids bound to hydrocarbon chains) can be decreased to approximately 10% of the volume of the vaccine.

According to a first advantageous embodiment, the molecular weight of the polymers is between 10 and 10,000 kD.

Advantageously, the molar ratio of hydrophobic constitutive repeating units and of the anionic constitutive repeating units is between 0.05 and 1.00 and, preferably between 0.10 and 0.40.

Preferably, the solubility of the polymers in water is at least 1 g/L.

According to another feature of the present invention, a process to obtain the polymer is described. The polymer can be obtained by one of the following processes:

1. copolymerization of anionic and hydrophobic monomers,
2. partial grafting of polymers,
3. partial hydrolysis of polymers, and
4. by an intermediate anhydride.

According to another preferred embodiment, a vaccine is proposed with a concentration of the polymer of 1–40 mg/mL of vaccine, preferably 4–24 mg/mL of vaccine, and more preferably 8–16 mg/mL of vaccine.

According to another aspect of the present invention, the vaccine comprises inactivated antigens of the Newcastle disease virus (NDV) and/or of the infectious bronchitis virus (IBV) for the vaccination of domestic animals.

The vaccines comprising an adjuvant based on polyacrylic acids bound to hydrocarbon chains are much more stable than the vaccines comprising an adjuvant based on a W/O or O/W emulsion, or based on water in mineral oil in water (W/O/W), because the adjuvant is a solution.

According to yet another feature of the present invention, the use of an aqueous solution of polymers is proposed, which has anionic constitutive repeating units and hydrophobic constitutive repeating units as adjuvant in vaccines.

According to another feature of the present invention, a method is provided to prepare a vaccine in solution, characterized in that an aqueous solution of an antigen and a polymer having anionic constitutive repeating units and hydrophobic constitutive repeating units are mixed.

EXAMPLE 1

Different water-soluble polymers according to the invention were synthesized by partial esterification of a polyacrylic acid with a molecular weight of 450,000 D (Carbopol 907 (PAA), Goodrich, Cleveland, Ohio, U.S.A.). In this application, the term "PAA" refers to "Carbopol 907." This polyacrylic acid was esterified with different hydroxyalkanes according to the method described by Cohen, H. L. in J. Poly. Sci., Vol. 14, pp. 7–22 (1976). The resulting polymers, hereafter called "alkyl-PAA," (see Table I) contain monomer units of the acrylic acid and monomer units of the alkyl acrylated type.

One gram of PAA was dissolved in 50 mL of the corresponding Alkanol and the solution was heated to 135° C. 50 $\mu$L of $H_2SO_4$ were added and the reaction mixture was maintained at 135° C. The reaction was stopped by rapid cooling of the reaction mixture and by adding one volume of distilled water. Then, the pH of the solution was adjusted to pH=6 and the solvents were evaporated at 80° C. at a reduced pressure ($10^{-6}$ b). The products so obtained were dissolved in distilled water, dialyzed against distilled water and then lyophilized.

The following compounds, whose principal properties are listed in Table I, were synthesized: decyl-PAA (C10-PAA), octyl-PAA (C8-PAA), butyl-PAA (C4-PAA), and methyl-PAA (C1-PAA).

The degree of esterification of these compounds was determined by NMR analysis. It is expressed in mol %.

The alkyl-PAAs were dissolved in a phosphate buffer (pH=7.5), with slight heating if necessary, and one volume of the adjuvant solution was mixed with one volume of the solution containing the antigen.

TABLE I

Principal properties of the synthesized alkyl-PAAs

| Product | MW PAA (kD) | Chain length | % ester (mol %) | Molar ratio (hydrophobic/anionic) |
|---|---|---|---|---|
| C8-PAA | 450 | C8 | 27 | 0.37 |
| C8-PAA | 450 | C8 | 12 | 0.14 |
| C8-PAA | 450 | C8 | 16 | 0.19 |
| C8-PAA | 450 | C8 | 16 | 0.19 |
| C4-PAA | 450 | C4 | 16 | 0.19 |
| C10-PAA | 450 | C10 | NT | NT |
| C8-PAA | 450 | C8 | 48 | 0.92 |
| C4-PAA | 450 | C4 tertiary | NT | NT |
| C1-PAA | 450 | C1 | 15 | 0.18 |

EXAMPLE 2

Hens were immunized by intramuscular injection (IM) with 0.5 mL of vaccine comprising the inactivated NDV (Newcastle disease virus) virus (Kimber strain) and the inactivated IBV (infectious bronchitis virus) virus, comprising the strains M41 and D274, (iNDV/iIBV) without adjuvant, at the age of four weeks, and then at the age of seven weeks, with the same antigens this time with an adjuvant.

The animals of the negative control group received phosphate buffered saline (PBS) solution instead of the adjuvant, and the animals of the positive control group were vaccinated with a vaccine comprising a standard adjuvant based on water in mineral oil.

Three weeks after the second vaccination, the hens were bled and in some experiments, blood samples were collected a second time several weeks later.

The blood samples were incubated at room temperature and after 2 h, the blood clots were eliminated, and the remaining cells are removed by centrifugation (10 min at 2700 G), and the serum samples of each animal were collected and stored at −20° C. until used.

96-well microtiter plates were saturated with purified NDV, the latter having been inactivated and diluted in a carbonate buffered solution (pH=9.6; 0.1M) for 2 h at 37° C. The plates were saturated with 5% (wt/vol) skim milk (SKM) in a carbonate buffer overnight at 4° C.

The Hen serum was treated with kaolin by incubating 1 volume of serum with 4 volumes of 25% (wt/vol) kaolin in a borate buffer (ICN Biomedicals, Inc., Costa Mesa, U.S.A.) for 30 min. The kaolin was then removed by centrifugation.

The serum of the hens was diluted 100 times in PBS containing 1% (wt/vol) bovine serum albumin (PBS/BSA). The serum samples are diluted in series two times in the same solution in 96-well plates and the plates are incubated for 1 to 2 h at 37° C. Hen anti-IgG, produced in goats, and coupled to peroxidase, in a 1/1000 dilution in PBS/SKM, are added, and the plates are incubated for 1–2 h at 37° C. The quantity of peroxidase in the plates was quantified by the addition of a substrate solution of ABTS+$H_2O_2$ (Kirkegaard & Perry Labs., U.S.A.) and the absorbance was measured at 405 nm using a multiscan Titertek.

The antibody titers are expressed in the form of 2-log values of the regression coefficient of the optical density plot with respect to the reciprocal dilution factor.

The antibody titer was also expressed by geometric means (value 2-log +/−SEM) and the antilog values of these averages ($2^{mean}$). The activity of the adjuvant was expressed as a percentage of increase, calculated as follows:

% increase=[antilog (sample)−antilog (negative control)]/[antilog (positive control)−antilog (negative control)]* 100.

Student's t-tests were carried out to analyze the statistical significance of these results, and the value $p>0.05$ was considered significant.

In four independent experiments, the adjuvant effect of one or more partially esterified polyacrylic acids was compared to the adjuvant effect of nonesterified PAA, and to a negative control group without adjuvant (PBS) and a positive control group with water in mineral oil (W/O).

The antibody titers were determined using the indirect ELISA method described above. The results of these experiments are listed in Table II.

TABLE II

Effects of different preparations of alkyl-PAA on the immune response against NDV/IBV, measured by indirect ELISA in hens

| Adjuvant [mg/ml] | n | Mean 2-log | SEM | antilog | Adjuvance % increase |
|---|---|---|---|---|---|
| Experiment I | | | | | |
| W/O | 40 | 9.6 | 0.7 | 776 | 100 |
| PBS | 40 | 5.6 | 1.0 | 49 | 0 |
| PAA [8] | 20 | 7.1 | 1.1 | 139 | 12 |
| PAA [40] | 20 | 6.8 | 1.0 | 110 | 8 |
| C8-PAA [8] | 20 | 9.0 | 0.6 | 491 | 61 |
| C8-PAA [40] | 20 | 9.3 | 0.8 | 630 | 80 |
| Experiment II | | | | | |
| W/O | 40 | 9.5 | 0.5 | 724 | 100 |
| PBS | 40 | 6.8 | 0.9 | 111 | 0 |
| PAA [8] | 20 | 7.4 | 1.0 | 162 | 8 |
| PAA [40] | 20 | 8.3 | 0.7 | 324 | 34 |
| C8-PAA [8] | 20 | 8.8 | 0.6 | 452 | 55 |
| C8-PAA [40] | 20 | 8.2 | 1.1 | 274 | 28 |
| C8-PAA [8] | 20 | 8.5 | 0.7 | 372 | 42 |
| C8-PAA [40] | 20 | 8.6 | 0.7 | 393 | 45 |
| C8-PAA [8] | 20 | 8.9 | 0.5 | 488 | 61 |
| C8-PAA [40] | 20 | 8.7 | 0.9 | 405 | 47 |
| Experiment III | | | | | |
| W/O | 40 | 8.9 | 0.9 | 477 | 100 |
| PBS | 40 | 5.7 | 0.6 | 52 | 0 |
| PAA [8] | 20 | 6.9 | 0.8 | 119 | 16 |
| PAA [24] | 20 | 7.3 | 0.7 | 158 | 25 |
| C8-PAA [8] | 20 | 8.4 | 0.7 | 338 | 69 |
| C8-PAA [8] | 20 | 8.3 | 0.7 | 315 | 64 |
| C8-PAA [24] | 20 | 8.3 | 0.5 | 315 | 64 |
| C8-PAA [8] | 20 | 9.1 | 0.3 | 549 | 121 |
| C8-PAA [8] | 20 | 8.4 | 0.5 | 338 | 69 |
| C8-PAA [24] | 20 | 8.0 | 0.6 | 256 | 49 |
| C8-PAA [8] | 20 | 8.8 | 0.6 | 446 | 96 |
| C8-PAA [24] | 20 | 8.6 | 0.5 | 388 | 81 |
| C8-PAA [8] | 20 | 7.1 | 0.7 | 137 | 20 |
| C8-PAA [24] | 20 | 5.8 | 0.6 | 56 | 0 |
| Experiment IV | | | | | |
| W/O | 40 | 8.6 | 1.0 | 388 | 100 |
| PBS | 40 | 5.2 | 1.1 | 37 | 0 |
| PAA [1] | 20 | 6.2 | 1.7 | 74 | 9 |
| PAA [2] | 20 | 6.0 | 1.0 | 64 | 6 |
| PAA [4] | 20 | 6.8 | 1.1 | 111 | 18 |
| PAA [8] | 20 | 7.2 | 1.0 | 147 | 26 |
| PAA [16] | 20 | 7.4 | 0.8 | 168 | 32 |
| C4-PAA [1] | 20 | 7.7 | 0.7 | 208 | 42 |
| C4-PAA [2] | 20 | 8.1 | 0.5 | 274 | 57 |
| C4-PAA [4] | 20 | 8.5 | 0.5 | 362 | 79 |
| C4-PAA [8] | 20 | 8.7 | 0.6 | 416 | 92 |
| C4-PAA [16] | 20 | 9.1 | 0.4 | 549 | 124 |
| C8-PAA [2] | 20 | 8.4 | 0.6 | 338 | 73 |
| C8-PAA [8] | 20 | 8.9 | 0.8 | 478 | 107 |
| C8-PAA [8] | 20 | 8.3 | 0.7 | 315 | 67 |
| *C4-PAA [8] | 20 | 7.3 | 0.9 | 158 | 29 |
| C1-PAA [8] | 20 | 8.2 | 0.7 | 294 | 62 | n = number of hens per group
SEM = standard deviation from the mean (standard error of mean)
*= C4 tertiary The positive and negative control groups yielded reproducible antibody titers in the four independent experiments and the antibody titers of the positive control were higher by three to four 2-log units (8–16 times) than those of the negative control group.

The (un-modified) PAA increased the titer of anti-iNDV antibodies between 6% and 32% (Experiments I–IV), and it seemed that this increase depends on the dose (Experiment IV). An optimal stimulation is obtained with a dose of 40 mg/mL (Experiment II).

The alkyl-PAA caused significantly higher responses than the unmodified PAA. The octyl-PAA and the butyl-PAA produced higher titers than decyl-PAA, t-butyl-PAA or methyl-PAA.

The maximum responses were obtained with doses of 8–40 mg/mL of octyl-PAA or of butyl-PAA. The responses were as high as the responses obtained with a standard adjuvant based on oil and water, used as positive control.

Experiment IV has shown that the response depends on the dose of modified PAA used, at least insofar as the butyl-PAA is concerned in the range of 1–16 mg/mL. Even at very low dosages—1–2 mg/mL—butyl-PAA significantly increased the humoral response. Titers of antibodies comparable to those encountered with much higher doses of unmodified PAA were obtained.

The humoral response increases with the dose of modified PAA used and it reaches a maximum which is equivalent to that caused by the standard adjuvants based on water and oil. Doses of 24–40 mg/mL of butyl-PAA and octyl-PAA occasionally induced weaker responses than doses of 8 mg/mL, indicating the existence of an optimal concentration for these compounds, which is 8–24 mg/mL.

EXAMPLE 3

The titers of anti-NDV antibodies in the individual serum samples were also determined using a commercially available anti-iNDV ELISA kit (Flockcheck Newcastle disease antibody test kit; IDEXX Labs, Inc., Maine, U.S.A.) according to the protocol.

The results of these analyses are listed in Table III.

TABLE III

Effect of different preparations of PAA on the titer of anti-iNDV antibodies measured by an IDEXX ELISA kit on hens

| Adjuvant [mg/ml] | n | mean 2-log | SEM | antilog | Adjuvance % Increase |
|---|---|---|---|---|---|
| Experiment I | | | | | |
| W/O | 40 | 14.5 | 0.7 | 23170 | 100 |
| PBS | 40 | 7.9 | 2.2 | 239 | 0 |
| PAA [8] | 20 | NT | | | |
| C8-PAA [8] | 20 | 13.7 | 0.8 | 13308 | 57 |
| C8-PAA [40] | 20 | 12.9 | 1.7 | 7643 | 32 |
| Experiment II | | | | | |
| W/O | 40 | 13.9 | 0.8 | 15268 | 100 |
| PBS | 40 | 8.7 | 1.9 | 416 | 0 |
| PAA [8] | 20 | 12.6 | 1.1 | 6209 | 39 |
| PAA [40] | 20 | NT | | | |
| C8-PAA [8] | 20 | 12.4 | 1.1 | 5404 | 36 |
| C8-PAA [40] | 20 | NT | | | |
| C8-PAA [8] | 20 | 12.3 | 1.5 | 5042 | 31 |
| C8-PAA [40] | 20 | 12.4 | 1.2 | 5404 | 36 |
| C8-PAA [8] | 20 | 12.5 | 1.0 | 5793 | 36 |
| C8-PAA [40] | 20 | 12.0 | 1.9 | 4096 | 25 |
| Experience III | | | | | |
| W/O | 40 | 13.1 | 1.3 | 8780 | 100 |
| PBS | 40 | 8.2 | 1.8 | 294 | 0 |
| PAA [8] | 20 | NT | | | |
| PAA [24] | 20 | NT | | | |
| C8-PAA [8] | 20 | 13.5 | 1.0 | 11585 | 133 |
| C8-PAA [8] | 20 | 12.8 | 1.1 | 7132 | 81 |
| C8-PAA [24] | 20 | 13.5 | 1.3 | 11585 | 133 |
| C8-PAA [8] | 20 | 13.7 | 0.6 | 13308 | 153 |
| C8-PAA [8] | 20 | 12.5 | 1.1 | 5793 | 65 |
| C4-PAA [24] | 20 | NT | | | |
| C4-PAA [8] | 20 | 13.7 | 1.2 | 13308 | 158 |
| C4-PAA [24] | 20 | 14.2 | 0.8 | 18820 | 218 |
| C10-PAA [8] | 20 | NT | | | |
| C10-PAA [24] | 20 | NT | | | |
| Experiment IV | | | | | |
| W/O | 40 | 12.9 | 1.6 | 7643 | 100 |
| PBS | 40 | 7.5 | 2.3 | 181 | 0 |
| PAA [1] | 20 | NT | | | |
| PAA [2] | 20 | NT | | | |
| PAA [4] | 20 | NT | | | |
| PAA [8] | 20 | NT | | | |
| PAA [16] | 20 | NT | | | |
| C4-PAA [1] | 20 | NT | | | |
| C4-PAA [2] | 20 | NT | | | |
| C4-PAA [4] | 20 | 13.4 | 1.0 | 10809 | 142 |
| C4-PAA [8] | 20 | 13.4 | 1.0 | 10809 | 142 |
| C4-PAA [16] | 20 | 13.8 | 0.9 | 14263 | 189 |
| C8-PAA [2] | 20 | NT | | | |
| C8-PAA [8] | 20 | 13.2 | 0.9 | 9410 | 124 |
| C8-PAA [8] | 20 | 12.0 | 1.6 | 4096 | 52 |
| *C4-PAA [8] | 20 | NT | | | |
| C1-PAA [8] | 20 | 12.2 | 1.4 | 4705 | 60 | n = number of hens per group
SEM = standard deviation from the mean (standard error of mean)
NT = not tested
*= C4 tertiary In the four experiments, the differences between the mean values of the negative controls were small. In the four experiments, the difference of the mean values of the positive controls were also small. The adjuvants of the modified PAAs 23–218%, butyl-PAA and octyl-PAA were more effective than methyl-PAA or decyl-PAA.

The results obtained by this method confirm those of the first method of analysis, which were specifically developed for these tests.

EXAMPLE 4

In 96-well plates, progressive dilutions of the antiserum were incubated with $10^6$ infectious particles (PFU) of a Kimber NDV strain for 18 h at 37° C. To each well, $10^5$ cells of the aviary line QT35 were added and put in plates. These plates were covered and incubated for an additional 48 h at 37° C. Serum dilutions producing a 50% reduction in the number of infectious particles were considered as being the antibody titer.

The results of these experiments are listed in Table IV.

TABLE IV

Effects of different preparations of PAA on the titer of anti-iNDV antibodies measured by virus neutralization (VN) on hens

| Adjuvant [mg/ml] | n | mean 2-log | SEM | antilog | Adjuvance % Increase |
|---|---|---|---|---|---|
| Experiment I | | | | | |
| W/O | 40 | 16.3 | 2.1 | 80684 | 100 |
| PBS | 40 | 8.1 | 1.8 | 274 | 0 |
| PAA [8] | 20 | 11.6 | 2.0 | 3104 | 4 |

TABLE IV-continued

Effects of different preparations of PAA on the titer of
anti-iNDV antibodies measured by virus neutralization (VN) on hens

| Adjuvant [mg/ml] | n | Titer of antibodies against NDV mean 2-log | SEM | antilog | Adjuvance % Increase |
|---|---|---|---|---|---|
| C8-PAA [8] | 20 | 15.1 | 2.4 | 35120 | 43 |
| C8-PAA [40] | 20 | 14.0 | 2.3 | 16384 | 20 |
| Experiment II | | | | | |
| W/O | 40 | 16.0 | 2.0 | 65536 | 100 |
| PBS | 40 | 11.1 | 2.0 | 2194 | 0 |
| PAA [8] | 20 | 11.5 | 1.8 | 2896 | 1 |
| PAA [40] | 20 | 13.0 | 2.2 | 8192 | 9 |
| C8-PAA [8] | 20 | 15.2 | 1.8 | 37641 | 56 |
| C8-PAA [40] | 20 | 11.4 | 2.9 | 2702 | 1 |
| C8-PAA [8] | 20 | 13.8 | 2.2 | 14263 | 19 |
| C8-PAA [40] | 20 | 14.7 | 2.0 | 26616 | 38 |
| C8-PAA [8] | 20 | 15.6 | 1.6 | 49667 | 75 |
| C8-PAA [40] | 20 | 13.7 | 3.0 | 13308 | 18 |
| Experiment III | | | | | |
| W/O | 40 | 16.2 | 1.0 | 75281 | 100 |
| PBS | 40 | 10.4 | 1.9 | 1351 | 0 |
| PAA [8] | 20 | 12.6 | 2.2 | 6208 | 8 |
| PAA [24] | 20 | 14.8 | 1.2 | 28526 | 37 |
| C8-PAA [8] | 20 | 15.4 | 1.7 | 43237 | 57 |
| C8-PAA [8] | 20 | 14.6 | 1.4 | 24834 | 32 |
| C8-PAA [24] | 20 | 15.9 | 0.8 | 61147 | 81 |
| C8-PAA [8] | 20 | 16.0 | 0.6 | 65536 | 87 |
| C8-PAA [8] | 20 | 15.5 | 1.4 | 46341 | 61 |
| C8-PAA [24] | 20 | 15.9 | 0.8 | 61147 | 81 |
| C4-PAA [8] | 20 | 16.1 | 0.6 | 70240 | 93 |
| C4-PAA [24] | 20 | 16.2 | 2.4 | 75281 | 100 |
| C10-PAA [8] | 20 | 13.3 | 1.7 | 10086 | 12 |
| C10-PAA [24] | 20 | 12.1 | 1.5 | 43900 | 58 |
| Experiment IV | | | | | |
| W/O | 40 | 15.4 | 2.0 | 43238 | 100 |
| PBS | 40 | 9.3 | 1.2 | 630 | 0 |
| PAA [1] | 20 | 10.9 | 2.8 | 1911 | 3 |
| PAA [2] | 20 | 10.2 | 1.1 | 1176 | 1 |
| PAA [4] | 20 | 11.0 | 1.3 | 2048 | 3 |
| PAA [8] | 20 | 12.1 | 1.6 | 4390 | 9 |
| PAA [16] | 20 | 12.6 | 1.3 | 6208 | 13 |
| C4-PAA [1] | 20 | 12.5 | 1.6 | 5793 | 12 |
| C4-PAA [2] | 20 | 14.1 | 1.1 | 17560 | 40 |
| C4-PAA [4] | 20 | 14.9 | 1.2 | 30574 | 70 |
| C4-PAA [8] | 20 | 14.7 | 1.2 | 26616 | 61 |
| C4-PAA [16] | 20 | 15.6 | 1.4 | 49667 | 115 |
| C8-PAA [2] | 20 | 14.3 | 1.1 | 20171 | 46 |
| C8-PAA [8] | 20 | 15.7 | 1.5 | 53232 | 123 |
| C8-PAA [8] | 20 | 14.0 | 1.2 | 16384 | 37 |
| *C4-PAA [8] | 20 | 12.0 | 1.3 | 4096 | 8 |
| C1-PAA [8] | 20 | 13.4 | 1.9 | 10809 | 24 | n = number of hens per group
SEM = standard deviation from the mean (standard error of mean)
*= C4 tertiary The animals of the negative and positive control groups produced reproducible antibody titers in the four independent experiments. The percentage of increase achieved by the unmodified PAA was 4–37% as a function of the dose of PAA used.

All the alkyl-PAA induced higher responses than the unmodified PAA.

The quality of the responses induced by the alkyl-PAA depended on the type of alkyl chain used and the degree of esterification of the PAA.

For butyl-PAA, a close relation between the dose of adjuvants and the humoral response (Experiment IV) was observed, whereas for octyl-PAA, the responses to a dose of 40 mg/mL did not always cause a higher response than weaker doses, indicating that the optimum quantity of octyl-PAA was between 24 mg/mL and 40 mg/mL.

The evaluation of the biological function of the antibodies, carried out by the virus neutralization (VN) test, showed a close correlation between the two ELISA tests and the VN test.

EXAMPLE 5

The adjuvance of the PAA was also tested on mice.

Groups of six mice were vaccinated with 25 µL of a vaccine comprising 1 volume of a solution of antigens consisting of 10 µg of inactivated influenza virus (strain MRC-11) and 1 mg of ovalbumin (OVA) (SIGMA, U.S.A.) per mL and one volume of adjuvant. Three weeks after the injection, the antibody titers were determined using the indirect ELISA method as described in Example 1.

The serum of the mice were prediluted in a 5% solution of skim milk in PBS (PBS/SKM). The serum samples were diluted in series two times in the same solution in 96-well plates, the plates were incubated for 1–2 h at 37° C. Mice anti-IgG, produced in goats and coupled to peroxidase, in a 1/300 dilution in PBS/BSA, were added, and the plates were incubated for 1–2 h at 37° C. The quantity of peroxidase in the plates was quantified using a substrate solution of ABTS+$H_2O_2$ (Kirkegaard & Perry Labs., U.S.A.) and the absorbance was measured at 405 nm using a multiscan Titertek.

The results of these experiments are listed in Table V.

TABLE V

Adjuvance of the alkyl-PAA on mice

| | | 2-log of the antibody titer against | | | |
|---|---|---|---|---|---|
| | | MRC11 | | OVA | |
| Adjuvant [mg/mL] | n | mean | SEM | mean | SEM |
| Experiment I | | | | | |
| PAA [4.0] | 6 | 11.2 | 0.5 | 9.0 | 0.6 |
| C8-PAA [4.0] | 6 | 14.8 | 0.3 | 10.1 | 0.4 |
| C8-PAA [4.0] | 6 | 14.5 | 0.8 | 9.5 | 0.6 |
| C8-PAA [4.0) | 6 | 13.6 | 1.1 | 8.7 | 0.8 |
| C4-PAA [4.0) | 6 | 14.3 | 0.4 | 9.4 | 1.1 |
| — | 6 | 10.0 | 0.4 | 4.2 | 0.9 |
| Experiment II | | | | | |
| PAA [4] | 6 | 15.0 | 0.5 | 8.8 | 0.8 |
| PAA [2] | 6 | 14.2 | 0.6 | 8.0 | 0.6 |
| C8-PAA [4] | 6 | 14.9 | 0.4 | 8.7 | 0.7 |
| C8-PAA [2] | 6 | 14.6 | 0.9 | 8.8 | 0.5 |
| C4-PAA [4] | 6 | 15.5 | 0.2 | 9.5 | 0.7 |
| C4-PAA [2] | 6 | 15.2 | 0.4 | 9.7 | 0.3 | n = number of hens [sic; mice] per group
SEM = standard deviation from the mean (standard error of mean)

The increase in the adjuvance of the PAA by the addition of aliphatic chains was only partially confirmed in mice, because the two independent experiments produced different effects.

EXAMPLE 6

Besides the adjuvance, other properties are important in evaluating a vaccine. They include the local reaction, which is an important aspect, although a certain level of reaction at the site of the injection is accepted in general by some animal species. The local toxicity was tested in vivo by monitoring the swelling of the paw of the mice after the injection of the vaccine into the pad of the mouse's paw. It has been shown that this method is very sensitive.

25 μL +/−5 μL of a vaccine containing 1 volume of an adjuvant diluted with 1 volume of an antigen solution containing 10 μg of MRC-11 and 1 mg of ovalbumin per mL of NaCl 0.9% (wt/vol) were injected (subcutaneously) into the sole of the left back foot of groups of six mice.

The thickness of the paw was measured one day before the injection and at different intervals after the injection using a semielectronic apparatus specifically designed for this purpose by the State University of Utrecht in the Netherlands. It has been shown that the precision of this apparatus is up to near 0.02 mm.

The swelling of the paw was calculated by obtaining the difference between the thickness before and after the treatment, expressed in 0.01 mm.

The results of these experiments are listed in Table VI.

TABLE VI

Reactogenicity of PAA and alkyl-PAA in mice.

Experiment I

| Adjuvant [mg/ml] | Mean swelling ($10^{-2}$ mm) Days | | | | | |
|---|---|---|---|---|---|---|
| | 1 | 2 | 6 | 10 | 17 | 22 |
| FAA [4] | 27 | 63 | 96 | 47 | 31 | 29 |
| C8-PAA [4] | 82 | 113 | 174 | 108 | 71 | 46 |
| C8-PAA [4] | 185 | 186 | 197 | 126 | 91 | 49 |
| C8-PAA [4] | 181 | 191 | 165 | 82 | 58 | 38 |
| C4-PAA [4] | 76 | 111 | 222 | 138 | 85 | 72 |
| C8-PAA [4] | 23 | 17 | 33 | 8 | 16 | 7 |
| PBS | 2 | 0 | 0 | 0 | 0 | 0 |

Experiment II

| Adjuvant [mg/mL] | Mean swelling ($10^{-2}$ mm) Days | | | | | | |
|---|---|---|---|---|---|---|---|
| | 1 | 2 | 3 | 7 | 12 | 20 | 6 | 35 |
| PAA [4] | 27 | 73 | 91 | 68 | 51 | 40 | 38 | 42 |
| PAA [2] | 33 | 52 | 36 | 37 | 30 | 19 | 14 | 14 |
| C8-PAA ]4] | 171 | 154 | 157 | 107 | 70 | 49 | 35 | 34 |
| C8-PAA [2] | 125 | 79 | 124 | 70 | 36 | 28 | 19 | 29 |
| C4-PAA ]4] | 72 | 77 | 135 | 120 | 88 | 68 | 59 | 61 |
| C4-PAA [2] | 105 | 80 | 74 | 84 | 62 | 38 | 42 | 69 |
| PBS | 3 | 0 | 0 | 0 | 0 | 0 | 0 | 0 |

The local toxicity of the PAA on the mice is moderate; the swelling of the paw of the mice reaches a maximum after a few days and it then gradually decreases after 2 or 3 weeks.

The addition of alkyl chains to the PAA increases the local reaction which, however, disappears after 2–5 weeks depending on the quantity injected. The octyl groups incite a stronger reaction than the butyl groups.

In contrast, the swelling caused by the injection of an adjuvant based on oil and water causes much greater swellings which persist for more than eight weeks.

What is claimed is:

1. An adjuvant for vaccines comprising an aqueous solution of a polymer having anionic constitutive repeating monomer units and hydrophobic constitutive repeating monomer units, characterized in that the monomer units to form the anionic constitutive repeating units are comprised of acrylic acid, and the monomer units to form the hydrophobic constitutive repeating units are selected from the group consisting of $C_4$–$C_8$ alkyl esters of acrylic acid wherein the concentration of said adjuvant in a vaccine is within the range of 1–40 mg/mL of a vaccine.

2. The adjuvant according to claim 1, characterized in that the monomer units to form the hydrophobic constitutive repeating units are selected from linear alkyl esters of acrylic acid whose alkyl group contains 4–8 carbon atoms.

3. The adjuvant according to claim 1, characterized in that the molar ratio of the hydrophobic constitutive repeating units to the anionic constitutive repeating units is between 0.05 and 1.00.

4. The adjuvant according to claim 1, characterized in that the molar ratio of the hydrophobic constitutive repeating units to the anionic constitutive repeating units is 0.10–0.40.

5. The adjuvant according to claim 1, characterized in that the molecular weight of the polymer is between 10–10,000 kD.

6. The adjuvant according to claim 1, characterized in that the said adjuvant is an aqueous solution, suspension or emulsion.

7. The adjuvant according to claim 1, characterized in that the polymer is water-soluble.

8. A vaccine comprising an immunogenic quantity of an antigen and an adjuvant according to one of claims 1 through 7.

9. The vaccine according to claim 8, characterized in that the concentration of the adjuvant is 4–24 mg/mL of the vaccine.

10. The vaccine according to claim 8, wherein the antigen comprises inactivated antigen of the Newcastle disease virus (NDV) and/or the infectious bronchitis virus (IBV) for the vaccination of domestic animals.

11. A method for the preparation of a vaccine in solution, characterized in that an aqueous mixture of an antigen and a polymer having hydrophobic constitutive repeating monomer units and anionic constitutive repeating monomer units are mixed wherein the monomer units comprising said anionic constitutive repeating units are comprised of acrylic acid and the monomer units comprising said hydrophobic constitutive repeating units are selected from the group consisting of $C_4$–$C_8$ alkyl esters of acrylic acid, wherein the concentration of said polymer is within the range of 1–40 mg/mL of the vaccine.

12. The adjuvant according to claim 2, characterized in that the monomer units to form the hydrophobic constitutive repeating units are selected from the group consisting of linear alkyl esters of acrylic acid whose alkyl group contains 4 and 8 carbon atoms.

13. The adjuvant according to claim 12, characterized in that the concentration of said adjuvant is 8–24 mg/mL of a vaccine.

14. The adjuvant according to claim 2, characterized in that said alkyl group contains 4 carbon atoms.

15. The adjuvant according to claim 14, characterized in that the concentration of said adjuvant is 1–24 mg/mL of a vaccine.

16. The adjuvant according to claim 15, characterized in that the concentration of said adjuvant is 8–24 mg/mL of a vaccine.

17. The adjuvant according to claim 2, characterized in that said alkyl group contains 8 carbon atoms.

18. The adjuvant according to claim 17, characterized in that the concentration of said adjuvant is 8–24 mg/mL of a vaccine.

* * * * *

UNITED STATES PATENT AND TRADEMARK OFFICE
CERTIFICATE OF CORRECTION

PATENT NO.   : 6,340,464 B1
DATED        : January 22, 2002
INVENTOR(S)  : Luuk Hilgers and Michel Strebelle It is certified that error appears in the above-identified patent and that said Letters Patent is hereby corrected as shown below:

<u>Column 1,</u>
Line 4, before "administered", please insert -- "An antigen is defined as a foreign substance which, when it is" --

Signed and Sealed this

Twentieth Day of August, 2002

Attest:

Attesting Officer

JAMES E. ROGAN
Director of the United States Patent and Trademark Office